(12) United States Patent
Mori et al.

(10) Patent No.: US 6,476,266 B1
(45) Date of Patent: Nov. 5, 2002

(54) DIAMINO COMPOUND AND PRODUCTION PROCESS FOR THE SAME

(75) Inventors: Takahiro Mori; Toshiya Sawai; Shizuo Murata; Masaaki Yazawa; Satoshi Tanioka; Kumiko Hara, all of Chiba (JP)

(73) Assignee: Chisso Corporation, Osaka (JP)

( * ) Notice: Subject to any disclaimer, the term of this patent is extended or adjusted under 35 U.S.C. 154(b) by 0 days.

(21) Appl. No.: 09/471,373

(22) Filed: Dec. 23, 1999

(30) Foreign Application Priority Data

Dec. 25, 1998 (JP) .......................................... 10-370026

(51) Int. Cl.⁷ ............................................. C07C 211/00

(52) U.S. Cl. ...................... 564/330; 564/305; 564/394; 564/419; 568/309; 568/329

(58) Field of Search ................................ 564/330, 305, 564/394, 419; 568/329, 309

(56) References Cited

U.S. PATENT DOCUMENTS

| | | | |
|---|---|---|---|
| 3,994,567 A | 11/1976 | Matsuo et al. | 350/160 LC |
| 4,661,254 A | 4/1987 | Zupancic et al. | 210/490 |
| 4,720,582 A | 1/1988 | Knöfel et al. | 564/305 |
| 4,849,130 A * | 7/1989 | Dabrowski et al. | |

FOREIGN PATENT DOCUMENTS

JP 51-65960 6/1976

* cited by examiner

Primary Examiner—Samuel Barts
(74) Attorney, Agent, or Firm—Wenderoth, Lind & Ponack, L.L.P.

(57) ABSTRACT

Provided is a diamino compound suitable for obtaining a polyimide which can form a liquid crystal alignment film capable of providing a liquid crystal display element, an intermediate therefor and a production process for the same. The above production process is characterized by reacting a cyclohexylbenzene derivative represented by Formula (3):

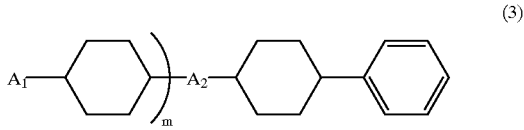

(3)

with an acid halide represented by Formula (4):

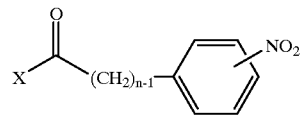

(4)

by the Frieldel-Crafts reaction to produce a cyclohexylphenylcarbonyl compound, and reducing the above compound after nitrating, whereby a compound represented by Formula (1) is obtained:

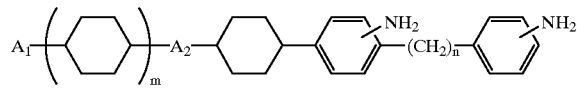

(1)

(wherein $A_1$ represents a hydrogen atom or an alkyl group having 1 to 12 carbon atoms; $A_2$ represents a single bond or an alkylene group having 1 to 5 carbon atoms, and one or optional methylene groups which are not adjacent in the group may be substituted with an oxygen atom; X is Br or Cl; m represents an integer of 0 to 3, and n represents an integer of 1 to 5).

7 Claims, 2 Drawing Sheets

DIAMINO COMPOUND AND PRODUCTION PROCESS FOR THE SAME

BACKGROUND OF THE INVENTION

1. Field of the Invention

The present invention relates to a diamino compound, an intermediate thereof and a production process for the same.

2. Description of the Related Art

A twist nematic (hereinafter abbreviated as TN) mode having a structure in which an aligning direction of nematic liquid crystal molecules is twisted by 90 degrees between electrode substrates which constitute a pair by two sheets is mainly adopted for a liquid crystal display element used for watches and electronic potable calculators. Further, a super twisted nematic (hereinafter abbreviated as STN) mode in which a twisted angle is increased to 180 to 300 degrees is developed as well, and a liquid crystal display element providing a good display quality as well in a large picture plane has come to be obtained.

Further, matrix display and color display have come to be prevailing in recent years, so that an MIM (metal-insulating phase-metal) element and a TFT (field effect type thin film transistor) element in which a lot of picture element electrodes and an active type twisted nematic mode capable of switching them on and off are adopted have come to be actively developed.

A problem which is common to all these modes is that caused is a phenomenon called burning in which another picture is displayed on a picture plane after displaying the same picture for long time and then the preceding picture remains thereon as an after-image. In particular, in order to obtain a liquid crystal display element having a high grade, it is a very important subject to prevent this burning phenomenon.

This burning is considered to be caused in such a manner that a direct current component applied to a liquid crystal display element produces an electric double layer due to an ion component of impurities contained in liquid crystal on the surface of an alignment film to bring about a deviation of charges between upper and lower substrates and this deviation, which is stably maintained, results in producing a potential difference. In particular, in a TFT element, a direct current component can not be removed due to the characteristics of the element, and therefore burning is liable to be more conspicuous than those of TN and STN elements and is serious.

Further, in order to prevent flickering on a picture plane due to an after-image, required in a TFT mode is an alignment film having a high voltage-holding rate even at 60 to 90° C. at which the voltage-holding rate is particularly notably reduced.

In a liquid crystal display element, a variation in a pretilt angle by heat leads to a change in a threshold voltage, and therefore a stability of the pretilt angle after a long-term reliability test at a high temperature is a very important element as well.

Organic base films of polyimide and polyamide are mainly used as an alignment film used for such liquid crystal display element, and it is described in Japanese Patent Application Laid-Open No. 65960/1976 that a polyesterimide polymer film is provided on an electrode substrate by a dimethyl acetamide solution of a polyamic acid which is a precursor of polyesterimide obtained by condensing 4,4'-diaminodiphenyl ether with an aromatic dicarboxylic anhydride obtained from trimellitic acid and hydroquinone and that this is subjected to aligning treatment to prepare a liquid crystal device. An element using a polyimide alignment film obtained by using such polyether compound is liable to cause burning.

SUMMARY OF THE INVENTION

An object of the present invention is to solve the problems described above and provide a diamino compound suitable for obtaining a polyimide capable of forming a liquid crystal alignment film capable of providing a liquid crystal display element which has a small burning phenomenon that is a small after-image and a high voltage-holding rate over a low temperature through a high temperature and which has a high pretilt angle and less change in the pretilt angle after a long-term reliability test at a high temperature, an intermediate therefor and a production process for the same.

Intensive research and development promoted by the present inventors have resulted in finding a diamino compound having such specific structure that, through burning and a voltage-holding rate are correlated with polarity on the surface of an alignment film, this polarity can be reduced. Further, they have found that an alignment film in which a burning phenomenon on the picture plane is reduced and a high voltage-holding rate is held over a low temperature through a high temperature and in which a variation in a pretilt angle is inhibited even after a long-term reliability test at a high temperature can obtained by using this diamino compound as a polyimide raw material for the alignment film. Thus, they have completed the present invention.

1) The diamino compound of the present invention is represented by Formula (1):

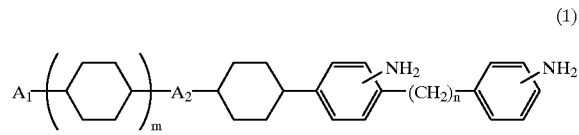

(1)

(wherein $A_1$ represents a hydrogen atom or a linear or branched alkyl group having 1 to 12 carbon atoms, and one or optional methylene groups which are not adjacent in the group may be substituted with an oxygen atom; $A_2$ represents a single bond or an alkylene group having 1 to 5 carbon atoms, and one. or optional methylene groups which are not adjacent in the group may be substituted with an oxygen atom; one amino group is bonded to any position in the ring; m represents an integer of 0 to 3, and n represents an integer of 1 to 5). It is preferably a diamino compound represented by the following Formula (1'):

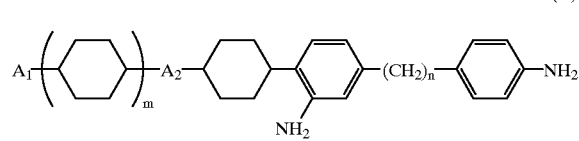

(1')

2) The diamino compound of the present invention which is more specifically shown is represented by Formula (2):

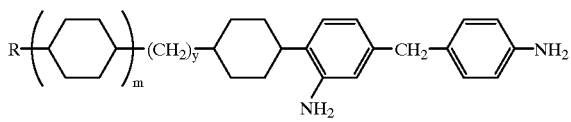

(2)

(wherein R represents a linear or branched alkyl group having 1 to 12 carbon atoms, an alkoxy group having 1 to 11 carbon atoms or a hydrogen atom; m represents an integer of 0 to 3, and y represents an integer of 0 to 5; and preferably, m is 1 to 2, and y is 0). It is more preferably a diamino compound represented by the following Formula (2'):

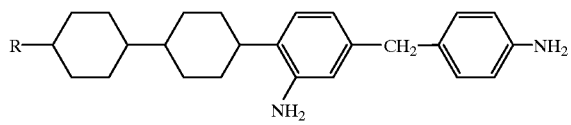

(2')

(wherein R represents a linear or branched alkyl group having 1 to 12 carbon atoms, an alkoxy group having 1 to 11 carbon atoms or a hydrogen atom).

3) A production process for the diamino compound of the present invention is characterized by reacting a cyclohexylbenzene derivative represented by Formula (3):

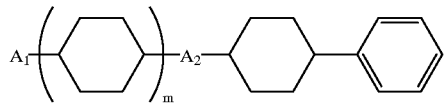

(3)

(wherein $A_1$ represents a hydrogen atom or a linear or branched alkyl group having 1 to 12 carbon atoms, and one or optional methylene groups which are not adjacent in the group may be substituted with an oxygen atom; $A_2$ represents a single bond or an alkylene group having 1 to 5 carbon atoms, and one or optional methylene groups which are not adjacent in the group may be substituted with an oxygen atom; and m represents an integer of 0 to 3) with an acid halide represented by Formula (4):

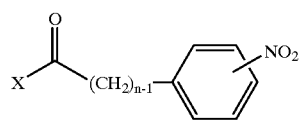

(4)

(wherein X represents any of a bromine atom and a chlorine atom; one nitro group is bonded to any position in the ring; and n represents an integer of 1 to 5) by the Frieldel-Crafts reaction to produce a cyclohexylphenylcarbonyl compound represented by Formula (5):

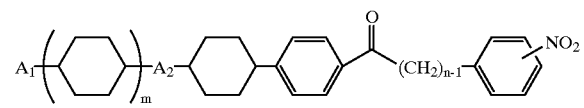

(5)

(wherein the respective marks are synonymous with those described above), and reducing the above compound after nitrating, whereby the compound represented by Formula (1):

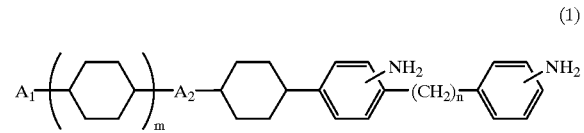

(1)

(wherein one amino group is bonded to any position in the ring, and the others are synonymous with those described above) is obtained.

A preferred method of the preceding reduction after nitration comprises nitrating the cyclohexylphenylcarbonyl compound represented by Formula (5) to synthesize a compound represented by Formula (6):

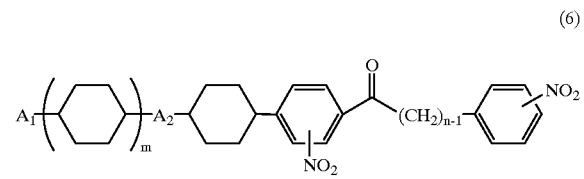

(6)

(wherein the respective marks are synonymous with those described above), then reducing the carbonyl group to thereby synthesize a dinitro compound represented by Formula (7):

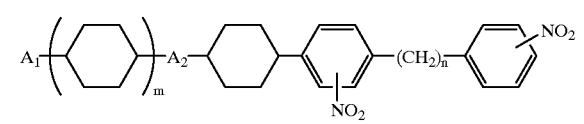

(7)

(wherein the substituents are synonymous with those described in Formula (6)), and reducing these nitro groups.

4) The cyclohexylphenylcarbonyl compound of the present invention is represented by Formula (5):

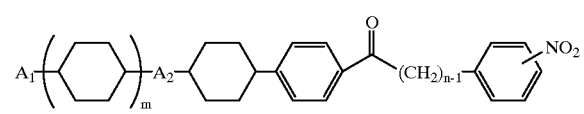

(5)

(wherein $A_1$ represents a hydrogen atom or a linear or branched alkyl group having 1 to 12 carbon atoms, and one or optional methylene groups which are not adjacent in the group may be substituted with an oxygen atom; $A_2$ represents a single bond or an alkylene group having 1 to 5 carbon atoms, and one or optional methylene groups which are not adjacent in the group may be substituted with an oxygen atom; one nitro group is bonded to any position in the ring; m represents an integer of 0 to 3, and n represents an integer of 1 to 5).

5) A production process for the cyclohexylphenylcarbonyl compound of the present invention is characterized by reacting the cyclohexylbenzene derivative represented by Formula (3):

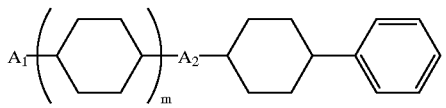

(3)

(wherein $A_1$ represents a hydrogen atom or a linear or branched alkyl group having 1 to 12 carbon atoms, and one or optional methylene groups which are not adjacent in the group may be substituted with an oxygen atom; $A_2$ represents a single bond or an alkylene group having 1 to 5 carbon atoms, and one or optional methylene groups which are not adjacent in the group may be substituted with an oxygen atom; and m represents an integer of 0 to 3) with the acid halide represented by Formula (4):

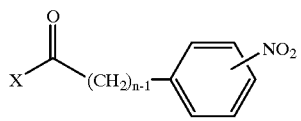

(4)

(wherein X represents any of a bromine atom and a chlorine atom; one nitro group is bonded to any position in the ring; and n represents an integer of 1 to 5) by the Frieldel-Crafts reaction to obtain the cyclohexylphenylcarbonyl compound represented by Formula (5):

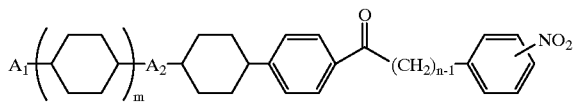

(5)

(wherein the respective marks are synonymous with those described above).

EMBODIMENT OF THE INVENTION

Figure 1:
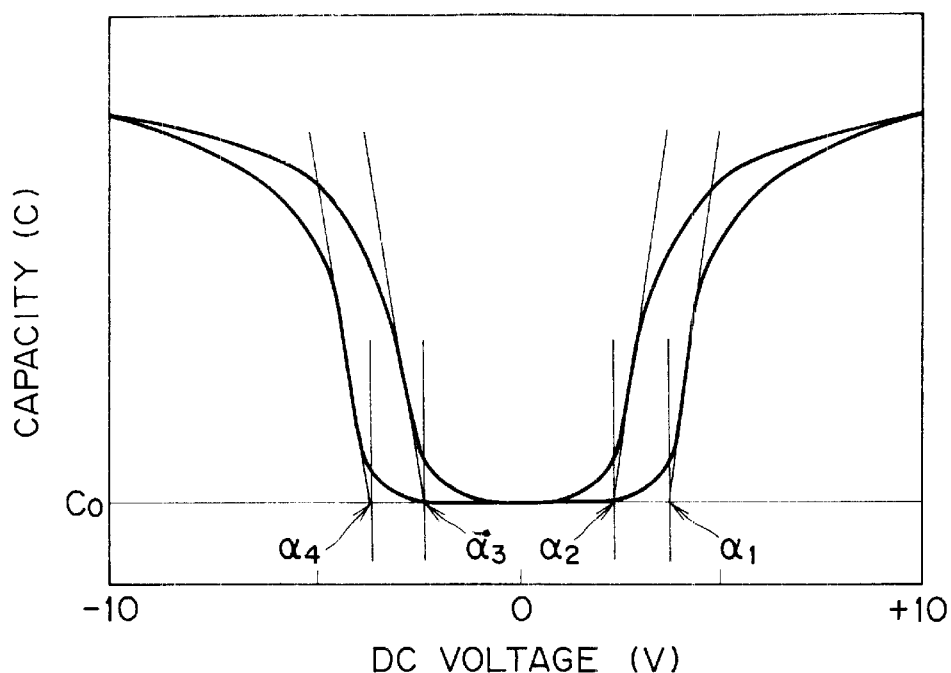
FIG. 1 is a drawing showing a C-V hysteresis curve.

The substituent $A_1$ in the diamino compound of the present invention represented by Formula (1) represents a hydrogen atom or a linear or branched alkyl group having 1 to 12 carbon atoms, and one or optional methylene groups which are not adjacent in the group may be substituted with an oxygen atom. It is preferably R shown in Formula (2) or (2') (represents a linear or branched alkyl group having 1 to 12 carbon atoms, an alkoxy group having 1 to 11 carbon atoms or a hydrogen atom). Further, the preferred specific examples thereof shall be shown below. The linear alkyl groups are shown in Table 1. The branched alkyl groups include: $(CH_3)_2CH$—, $(CH_3)_2CHCH_2$—, $(CH_3)_2CH(CH_2)_2$—, $(CH_3)_2CH(CH_2)_3$—, $(CH_3)_2CH(CH_2)_4$—, $(CH_3)_2CH(CH_2)_5$—, $(CH_3)_2CH(CH_2)_6$—, $(CH_3)_2CH(CH_2)_7$—, $(CH_3)_2CH(CH_2)_8$— and $(CH_3)_2CH(CH_2)_9$—.

The groups containing oxygen atoms include: $CH_3O$—, $C_2H_5O$—, $C_3H_7O$—, $C_4H_9O$—, $C_5H_{11}O$—, $C_6H_{13}O$—, $C_7H_{15}O$—, $C_8H_{17}O$—, $C_9H_{19}O$—, $C_{10}H_{21}O$— and $C_{11}H_{23}O$—. However, they are not all.

Further, the substituent $A_2$ represents a single bond or an alkylene group having 1 to 5 carbon atoms, and one or optional methylene groups which are not adjacent in the group may be substituted with an oxygen atom. The preferred specific examples thereof are shown in Table 1.

The specific examples of the diamino compound of the present invention represented by Formula (1) shall be shown by formulas represented by acronyms. The acronyms shown here are defined as shown in Table 1.

TABLE 1

| Left terminal group | Acronyms | Right terminal group | Acronyms |
|---|---|---|---|
| cyclohexyl— | H | —phenyl-$H_2N$ | B(1A) |
| $CH_3$— | 1 | —phenyl-$NH_2$ | B(2A) |

TABLE 1-continued

| | | | |
|---|---|---|---|
| C₂H₅— | 2 | [structure: methyl-aniline with NH₂] | B(3A) |
| C₃H₇— | 3 | [structure: methylbenzene] | B |
| C₄H₉— | 4 | | |
| C₅H₁₁— | 5 | | |
| C₆H₁₃— | 6 | | |
| C₇H₁₅— | 7 | | |
| C₈H₁₇— | 8 | | |
| C₉H₁₉— | 9 | | |
| C₁₀H₂₁— | 10 | | |
| C₁₁H₂₃— | 11 | | |
| C₁₂H₂₅— | 12 | | |

| Bonding Group | Acronyms | Bonding group | Acronyms |
|---|---|---|---|
| —CH₂— | 1 | [cyclohexyl] | H |
| —C₂H₄— | 2 | [cyclohexyl-phenyl-NH₂] | HB(4A) |
| —C₃H₆— | 3 | | HB(5A) |
| —C₄H₈— | 4 | | |
| —C₅H₁₀— | 5 | | |
| —O— | 0 | | |

Representation examples

5HHB(4A)1B(3A)

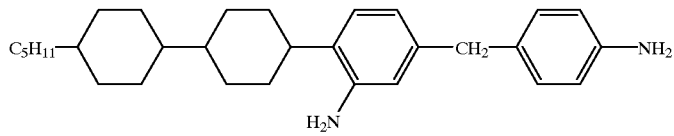

5H2HB(4A)1B(3A)

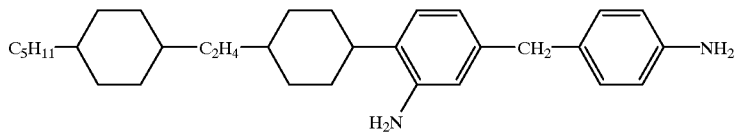

3HHHB(4A)1B(3A)

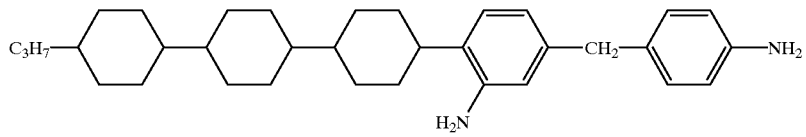

Included are:
1HB(4A)1B(3A)
5HB(4A)1B(3A)
7HB(4A)1B(3A)
8HB(4A)1B(3A)
4HHB(4A)1B(3A)
5HHB(4A)1B(3A)
7HHB(4A)1B(3A)
3HHHB(4A)1B(3A)
5HHHB(4A)1B(3A)

10HHHB(4A)1B(3A)
1HHHHB(4A)1B(3A)
5HHHHB(4A)1B(3A)
7HHHHB(4A)1B(3A)
12HHHHB(4A)1B(3A)
4H1HB(4A)1B(3A)
5H1HB(4A)1B(3A)
6H1HB(4A)1B(3A)
7H1HB(4A)1B(3A)
2HH1HB(4A)1B(3A)
5HH1HB(4A)1B(3A)
7HH1HB(4A)1B(3A)
3HHH1HB(4A)1B(3A)
5HHH1HB(4A)1B(3A)
10HHH1HB(4A)1B(3A)
3HOHB(4A)1B(3A)
5HHOHB(4A)1B(3A)
7HHHOHB(4A)1B(3A)
3H2HB(4A)1B(3A)
5H2HB(4A)1B(3A)
7H2HB(4A)1B(3A)
4HH2HB(4A)1B(3A)
5HH2HB(4A)1B(3A)
8HH2HB(4A)1B(3A)
3HHH2HB(4A)1B(3A)
5HHH2HB(4A)1B(3A)
9HHH2HB(4A)1B(3A)
3H3HB(4A)1B(3A)
5H3HB(4A)1B(3A)
8H3HB(4A)1B(3A)
HH3HB(4A)1B(3A)
5HH3HB(4A)1B(3A)
7HH3HB(4A)1B(3A)
2HHH3HB(4A)1B(3A)
6HHH3HB(4A)1B(3A)
11HHH3HB(4A)1B(3A)
3H4HB(4A)1B(3A)
5H4HB(4A)1B(3A)
8H4HB(4A)1B(3A)
2HH4HB(4A)1B(3A)
5HH4HB(4A)1B(3A)
7HH4HB(4A)1B(3A)
3HHH4HB(4A)1B(3A)
7HHH4HB(4A)1B(3A)
12HHH4HB(4A)1B(3A)
H5HB(4A)1B(3A)
3H5HB(4A)1B(3A)
5H5HB(4A)1B(3A)
1HH5HB(4A)1B(3A)
7HH5HB(4A)1B(3A)
10HH5HB(4A)1B(3A)
3HHH5HB(4A)1B(3A)
5HHH5HB(4A)1B(3A)
7HHH5HB(4A)1B(3A)
5HHB(5A)1B(1A)
7HHHB(5A)1B(2A)
4H1HB(5A)1B(1A)
5H2HB(5A)1B(2A)
10HH2HB(5A)1B(1A)
6H3HB(5A)1B(2A)
3HHH3HB(5A)1B(1A)
5HB(4A)2B(3A)
6HB(4A)2B(3A)
7HB(4A)2B(3A)
2HHB(4A)2B(3A)
4HHB(4A)2B(3A)
9HHB(4A)2B(3A)
3HHHB(4A)2B(3A)
5HHHB(4A)2B(3A)
7HHHB(4A)2B(3A)
2HHHB(4A)2B(3A)
6HHHHB(4A)2B(3A)
12HHHHB(4A)2B(3A)
3H1HB(4A)2B(3A)
4H1HB(4A)2B(3A)
8H1HB(4A)2B(3A)
5HH1HB(4A)2B(3A)
6HH1HB(4A)2B(3A)
7HH1HB(4A)2B(3A)
3HHH1HB(4A)2B(3A)
9HHH1HB(4A)2B(3A)
12HHH1HB(4A)2B(3A)
3HOHB(4A)2B(3A)
5HHOHB(4A)2B(3A)
8HHHOHB(4A)2B(3A)
3H2HB(4A)2B(3A)
4H2HB(4A)2B(3A)
6H2HB(4A)2B(3A)
5HH2HB(4A)2B(3A)
7HH2HB(4A)2B(3A)
10HH2HB(4A)2B(3A)
1HHH2HB(4A)2B(3A)
2HHH2HB(4A)2B(3A)
3HHH2HB(4A)2B(3A)
5H3HB(4A)2B(3A)
7H3HB(4A)2B(3A)
9H3HB(4A)2B(3A)
2HH3HB(4A)2B(3A)
4HH3HB(4A)2B(3A)
5HH3HB(4A)2B(3A)
3HHH3HB(4A)2B(3A)
6HHH3HB(4A)2B(3A)
7HHH3HB(4A)2B(3A)
2H4HB(4A)2B(3A)
6H4HB(4A)2B(3A)
7H4HB(4A)2B(3A)
3HH4HB(4A)2B(3A)
5HH4HB(4A)2B(3A)
7HH4HB(4A)2B(3A)
2HHH4HB(4A)2B(3A)
7HHH4HB(4A)2B(3A)
12HHH4HB(4A)2B(3A)
3H5HB(4A)2B(3A)
5H5HB(4A)2B(3A)
7H5HB(4A)2B(3A)
4HH5HB(4A)2B(3A)
6HH5HB(4A)2B(3A)
9HH5HB(4A)2B(3A)
3HHH5HB(4A)2B(3A)
5HHH5HB(4A)2B(3A)
7HHH5HB(4A)2B(3A)
2H1HB(5A)2B(2A)
4HH2HB(5A)2B(2A)
4HH3HB(5A)2B(1A)
5HHH1HB(5A)2B(2A)
10HH5HB(5A)2B(1A)
HHH1HB(5A)2B(2A)
3HB(4A)3B(3A)
4HB(4A)3B(3A)
5HB(4A)3B(3A)
3HHB(4A)3B(3A)
5HHB(4A)3B(3A)
7HHB(4A)3B(3A)
5HHHB(4A)3B(3A)

6HHHB(4A)3B(3A)
9HHHB(4A)3B(3A)
HHHHB(4A)3B(3A)
5HHHHB(4A)3B(3A)
7HHHHB(4A)3B(3A)
2H1HB(4A)3B(3A)
4H1HB(4A)3B(3A)
7H1HB(4A)3B(3A)
3HH1HB(4A)3B(3A)
5HH1HB(4A)3B(3A)
7HH1HB(4A)3B(3A)
HHH1HB(4A)3B(3A)
4HHH1HB(4A)3B(3A)
9HHH1HB(4A)3B(3A)
2H2HB(4A)3B(3A)
5H2HB(4A)3B(3A)
11H2HB(4A)3B(3A)
5HH2HB(4A)3B(3A)
6HH2HB(4A)3B(3A)
8HH2HB(4A)3B(3A)
1HHH2HB(4A)3B(3A)
3HHH2HB(4A)3B(3A)
5HHH2HB(4A)3B(3A)
4H3HB(4A)3B(3A)
5H3HB(4A)3B(3A)
6H3HB(4A)3B(3A)
5HH3HB(4A)3B(3A)
7HH3HB(4A)3B(3A)
9HH3HB(4A)3B(3A)
4HHH3HB(4A)3B(3A)
5HHH3HB(4A)3B(3A)
8HHH3HB(4A)3B(3A)
3H4HB(4A)3B(3A)
6H4HB(4A)3B(3A)
10H4HB(4A)3B(3A)
3HH4HB(4A)3B(3A)
5HH4HB(4A)3B(3A)
9HH4HB(4A)3B(3A)
1HHH4HB(4A)3B(3A)
5HHH4HB(4A)3B(3A)
8HHH4HB(4A)3B(3A)
2H5HB(4A)3B(3A)
5H5HB(4A)3B(3A)
8H5HB(4A)3B(3A)
3HH5HB(4A)3B(3A)
5HH5HB(4A)3B(3A)
11HH5HB(4A)3B(3A)
2HHH5HB(4A)3B(3A)
6HHH5HB(4A)3B(3A)
7HHH5HB(4A)3B(3A)
2H1HB(5A)3B(2A)
4HH1HB(5A)3B(1A)
7H2HB(5A)3B(1A)
6HH2HB(5A)3B(1A)
10HHHB(5A)3B(2A)
5H5HB(5A)3B(2A)
3HB(4A)4B(3A)
5HB(4A)4B(3A)
8HB(4A)4B(3A)
5HHB(4A)4B(3A)
7HHB(4A)4B(3A)
10HHB(4A)4B(3A)
3HHHB(4A)4B(3A)
6HHHB(4A)4B(3A)
12HHHB(4A)4B(3A)
2HHHHB(4A)4B(3A)
6HHHHB(4A)4B(3A)
7HHHHB(4A)4B(3A)
3H1HB(4A)4B(3A)
6H1HB(4A)4B(3A)
8H1HB(4A)4B(3A)
HH1HB(4A)4B(3A)
2HH1HB(4A)4B(4A)
5HH1HB(4A)4B(4A)
3HHH1HB(4A)4B(4A)
5HHH1HB(4A)4B(4A)
10HHH1HB(4A)4B(4A)
3H2HB(4A)4B(4A)
5H2HB(4A)4B(4A)
7H2HB(4A)4B(4A)
4HH2HB(4A)4B(4A)
5HH2HB(4A)4B(4A)
6HH2HB(4A)4B(4A)
5HHH2HB(4A)4B(4A)
8HHH2HB(4A)4B(4A)
12HHH2HB(4A)4B(4A)
1H3HB(4A)4B(3A)
4H3HB(4A)4B(3A)
7H3HB(4A)4B(3A)
3HH3HB(4A)4B(3A)
5HH3HB(4A)4B(3A)
8HH3HB(4A)4B(3A)
1HHH3HB(4A)4B(3A)
6HHH3HB(4A)4B(3A)
11HHH3HB(4A)4B(3A)
3H4HB(4A)4B(3A)
4H4HB(4A)4B(3A)
8H4HB(4A)4B(3A)
2HH4HB(4A)4B(3A)
5HH4HB(4A)4B(3A)
7HH4HB(4A)4B(3A)
4HHH4HB(4A)4B(3A)
5HHH4HB(4A)4B(3A)
9HHH4HB(4A)4B(3A)
H5HB(4A)4B(3A)
3H5HB(4A)4B(3A)
7H5HB(4A)4B(3A)
2HH5HB(4A)4B(3A)
4HH5HB(4A)4B(3A)
7HH5HB(4A)4B(3A)
3HHH5HB(4A)4B(3A)
6HHH5HB(4A)4B(3A)
9HHH5HB(4A)4B(3A)
3OH1HB(4A)4B(3A)
5OHH1HB(4A)4B(3A)
6OH2HB(4A)4B(3A)
7OHH2HB(4A)4B(3A)
1OHHH1HB(4A)4B(3A)
11OHH4HB(4A)4B(3A)
1HB(4A)5B(3A)
4HB(4A)5B(3A)
5HB(4A)5B(3A)
3HHB(4A)5B(3A)
5HHB(4A)5B(3A)
7HHB(4A)5B(3A)
4HHHB(4A)5B(3A)
7HHHB(4A)5B(3A)
10HHHB(4A)5B(3A)
3HHHHB(4A)5B(3A)
4HHHHB(4A)5B(3A)
5HHHHB(4A)5B(3A)
1H1HB(4A)5B(3A)
5H1HB(4A)5B(3A)
9H1HB(4A)5B(3A)

3HH1HB(4A)5B(3A)
5HH1HB(4A)5B(3A)
11HH1HB(4A)5B(3A)
2HHH1HB(4A)5B(3A)
6HHH1HB(4A)5B(3A)
8HHH1HB(4A)5B(3A)
3H2HB(4A)5B(3A)
5H2HB(4A)5B(3A)
7H2HB(4A)5B(3A)
HH2HB(4A)5B(3A)
4HH2HB(4A)5B(3A)
7HH2HB(4A)5B(3A)
3HHH2HB(4A)5B(3A)
6HHH2HB(4A)5B(3A)
9HHH2HB(4A)5B(3A)
4H3HB(4A)5B(3A)
5H3HB(4A)5B(3A)
8H3HB(4A)5B(3A)
2HH3HB(4A)5B(3A)
6HH3HB(4A)5B(3A)
7HH3HB(4A)5B(3A)
5HHH3HB(4A)5B(3A)
6HHH3HB(4A)5B(3A)
9HHH3HB(4A)5B(3A)
3H4HB(4A)5B(3A)
7H4HB(4A)5B(3A)
9H4HB(4A)5B(3A)
2HH4HB(4A)5B(3A)
3HH4HB(4A)5B(3A)
7HH4HB(4A)5B(3A)
3HHH4HB(4A)5B(3A)
5HHH4HB(4A)5B(3A)
7 HHH4HB(4A)5B(3A)
4H5HB(4A)5B(3A)
6H5HB(4A)5B(3A)
9H5HB(4A)5B(3A)
1HH5HB(4A)5B(3A)
5HH5HB(4A)5B(3A)
10HH5HB(4A)5B(3A)
3HHH5HB(4A)5B(3A)
7HHH5HB(4A)5B(3A)
11HHH5HB(4A)5B(3A)
3OH1HB(4A)5B(3A)
5OH1HB(4A)5B(3A)
6OHH2HB(4A)5B(3A)
8OHH5HB(4A)5B(3A)
10OH2HB(4A)5B(3A)
1OHHH1HB(4A)5B(3A)

Among them, the specific examples of the preferred compounds include:
1HB(4A)1B(3A)
5HB(4A)1B(3A)
7HB(4A)1B(3A)
1OHB(4A)1B(3A)
3OHB(4A)1B(3A)
7OHB(4A)2B(3A)
5OHB(4A)3B(3A)
4HHB(4A)1B(3A)
5HHB(4A)1B(3A)
7HHB(4A)1B(3A)
1OHHB(4A)1B(3A)
2OHHB(4A)2B(3A)
5OHHHB(4A)1B(3A)
7OH2HB(4A)3B(3A)
3HHHB(4A)1B(3A)
5HHHB(4A)1B(3A)
10HHHB(4A)1B(3A)
1HHHHB(4A)1B(3A)
5HHHHB(4A)1B(3A)
7HHHHB(4A)1B(3A)
4H1HB(4A)1B(3A)
5H1HB(4A)1B(3A)
7H1HB(4A)1B(3A)
2HH1HB(4A)1B(3A)
5HH1HB(4A)1B(3A)
7HH1HB(4A)1B(3A)
3HHH1HB(4A)1B(3A)
5HHH1HB(4A)1B(3A)
3H2HB(4A)1B(3A)
5H2HB(4A)1B(3A)
7H2HB(4A)1B(3A)
4HH2HB(4A)1B(3A)
5HH2HB(4A)1B(3A)
8HH2HB(4A)1B(3A)
3HHH2HB(4A)1B(3A)
5HHH2HB(4A)1B(3A)
9HHH2HB(4A)1B(3A)
5HB(4A)2B(3A)
6HB(4A)2B(3A)
7HB(4A)2B(3A)
2HHB(4A)2B(3A)
4HHB(4A)2B(3A)
9HHB(4A)2B(3A)
3HHHB(4A)2B(3A)
5HHHB(4A)2B(3A)
7HHHB(4A)2B(3A)
2HHHHB(4A)2B(3A)
6HHHHB(4A)2B(3A)
3H1HB(4A)2B(3A)
4H1HB(4A)2B(3A)
8H1HB(4A)2B(3A)
5HH1HB(4A)2B(3A)
6HH1HB(4A)2B(3A)
7HH1HB(4A)2B(3A)
3HHH1HB(4A)2B(3A)
9HHH1HB(4A)2B(3A)
12HHH1HB(4A)2B(3A)
3H2HB(4A)2B(3A)
4H2HB(4A)2B(3A)
6H2HB(4A)2B(3A)
5HH2HB(4A)2B(3A)
7HH2HB(4A)2B(3A)
10HH2HB(4A)2B(3A)
1HHH2HB(4A)2B(3A)
2HHH2HB(4A)2B(3A)
3HHH2HB(4A)2B(3A)
3HB(4A)3B(3A)
4HB(4A)3B(3A)
5HB(4A)3B(3A)
3HHB(4A)3B(3A)
5HHB(4A)3B(3A)
7HHB(4A)3B(3A)
5HHHB(4A)3B(3A)
6HHHB(4A)3B(3A)
9HHHB(4A)3B(3A)
HHHHB(4A)3B(3A)
5HHHHB(4A)3B(3A)
7HHHHB(4A)3B(3A)
2H1HB(4A)3B(3A)
4H1HB(4A)3B(3A)
7H1HB(4A)3B(3A)
3HH1HB(4A)3B(3A)
5HH1HB(4A)3B(3A)
7HH1HB(4A)3B(3A)

HHH1HB(4A)3B(3A)
4HHH1HB(4A)3B(3A)
9HHH1HB(4A)3B(3A)
2H2HB(4A)3B(3A)
5H2HB(4A)3B(3A)
11H2HB(4A)3B(3A)
5HH2HB(4A)3B(3A)
6HH2HB(4A)3B(3A)
8HH2HB(4A)3B(3A)
1HHH2HB(4A)3B(3A)
3HHH2HB(4A)3B(3A)
5HHH2HB(4A)3B(3A)
3HB(4A)4B(3A)
5HB(4A)4B(3A)
8HB(4A)4B(3A)
5HHB(4A)4B(3A)
7HHB(4A)4B(3A)
10HHB(4A)4B(3A)
3HHHB(4A)4B(3A)
6HHHB(4A)4B(3A)
12HHHB(4A)4B(3A)
2HHHHB(4A)4B(3A)
6HHHHB(4A)4B(3A)
7HHHHB(4A)4B(3A)
3H1HB(4A)4B(3A)
6H1HB(4A)4B(3A)
8H1HB(4A)4B(3A)
HH1HB(4A)4B(3A)
2HH1HB(4A)4B(4A)
5HH1HB(4A)4B(4A)
3HHH1HB(4A)4B(4A)
5HHH1HB(4A)4B(4A)
3H2HB(4A)4B(4A)
5H2HB(4A)4B(4A)
7H2HB(4A)4B(4A)
4HH2HB(4A)4B(4A)
5HH2HB(4A)4B(4A)
6HH2HB(4A)4B(4A)
5HHH2HB(4A)4B(4A)
8HHH2HB(4A)4B(4A)
12HHH2HB(4A)4B(4A)
1HB(4A)5B(3A)
4HB(4A)5B(3A)
5HB(4A)5B(3A)
3HHB(4A)5B(3A)
5HHB(4A)5B(3A)
7HHB(4A)5B(3A)
4HHHB(4A)5B(3A)
7HHHB(4A)5B(3A)
10HHHB(4A)5B(3A)
3HHHHB(4A)5B(3A)
4HHHHB(4A)5B(3A)
5HHHHB(4A)5B(3A)
1H1HB(4A)5B(3A)
5H1HB(4A)5B(3A)
9H1HB(4A)5B(3A)
3HH1HB(4A)5B(3A)
5HH1HB(4A)5B(3A)
11HH1HB(4A)5B(3A)
2HHH1HB(4A)5B(3A)
6HHH1HB(4A)5B(3A)
8HHH1HB(4A)5B(3A)
3H2HB(4A)5B(3A)
5H2HB(4A)5B(3A)
7H2HB(4A)5B(3A)
HH2HB(4A)5B(3A)
4HH2H B(4A)5B(3A)
7HH2HB(4A)5B(3A)
3HHH2HB(4A)5B(3A)
6HHH2HB(4A)5B(3A)
9HHH2HB(4A)5B(3A)

Among them, the specific examples of the preferred compounds include:
1HB(4A)1B(3A)
5HB(4A)1B(3A)
7HB(4A)1B(3A)
4HHB(4A)1B(3A)
5HHB(4A)1B(3A)
7HHB(4A)1B(3A)
3HHHB(4A)1B(3A)
5HHHB(4A)1B(3A)
10HHHB(4A)1B(3A)
1HHHHB(4A)1B(3A)
5HHHHB(4A)1B(3A)
7HHHHB(4A)1B(3A)
4H1HB(4A)1B(3A)
5H1HB(4A)1B(3A)
7H1HB(4A)1B(3A)
2HH1HB(4A)1B(3A)
5HH1HB(4A)1B(3A)
7HH1HB(4A)1B(3A)
3HHH1HB(4A)1B(3A)
5HHH1HB(4A)1B(3A)
3H2HB(4A)1B(3A)
5H2HB(4A)1B(3A)
7H2HB(4A)1B(3A)
4HH2HB(4A)1B(3A)
5HH2HB(4A)1B(3A)
8HH2HB(4A)1B(3A)
3HHH2HB(4A)1B(3A)
5HHH2HB(4A)1B(3A)
9HHH2HB(4A)1B(3A)
5HB(4A)2B(3A)
6HB(4A)2B(3A)
7HB(4A)2B(3A)
2HHB(4A)2B(3A)
4HHB(4A)2B(3A)
9HHB(4A)2B(3A)
3HHHB(4A)2B(3A)
5HHHB(4A)2B(3A)
7HHHB(4A)2B(3A)
2HHHHB(4A)2B(3A)
6HHHHB(4A)2B(3A)
3H1HB(4A)2B(3A)
4H1HB(4A)2B(3A)
8H1HB(4A)2B(3A)
5HH1HB(4A)2B(3A)
6HH1HB(4A)2B(3A)
7HH1HB(4A)2B(3A)
3HHH1HB(4A)2B(3A)
9HHH1HB(4A)2B(3A)
12HHH1HB(4A)2B(3A)
3H2HB(4A)2B(3A)
4H2HB(4A)2B(3A)
6H2HB(4A)2B(3A)
5HH2HB(4A)2B(3A)
7HH2HB(4A)2B(3A)
10HH2HB(4A)2B(3A)
1HHH2HB(4A)2B(3A)
2HHH2HB(4A)2B(3A)
3HHH2HB(4A)2B(3A)

The cyclohexylphenylcarbonyl compound which is the intermediate for the diamino compound of the present invention is a compound represented by Formula (5). The specific examples thereof shall be shown by formulas represented by acronyms. The acronyms shown here are defined as shown in Table 2.

TABLE 2

| Left terminal group | Acronyms | Right terminal group | Acronyms |
|---|---|---|---|
| cyclohexyl— | H | 2-nitrophenyl | B(1N) |
| $CH_3$— | 1 | 3-nitrophenyl | B(2N) |
| $C_2H_5$— | 2 | 4-nitrophenyl | B(3N) |
| $C_3H_7$— | 3 | cyclohexyl-phenyl-C(=O)– | B |
| $C_4H_9$— | 4 | | |
| $C_5H_{11}$— | 5 | | |
| $C_6H_{13}$— | 6 | | |
| $C_7H_{15}$— | 7 | | |
| $C_8H_{17}$— | 8 | | |
| $C_9H_{19}$— | 9 | | |
| $C_{10}H_{21}$— | 10 | | |
| $C_{11}H_{23}$— | 11 | | |
| $C_{12}H_{25}$— | 12 | | |

| Bonding Group | Acronyms | Bonding group | Acronyms |
|---|---|---|---|
| —$CH_2$— | 1 | cyclohexyl | H |
| —$C_2H_4$— | 2 | cyclohexyl-phenyl-C(=O)– | HBK |
| —$C_3H_6$— | 3 | cyclohexyl-phenyl-NH$_2$ | HB(5A) |
| —$C_4H_8$— | 4 | | |
| —O— | 0 | | |

Representation examples

5HHBKB(3N)

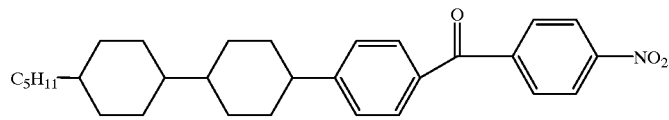

7H2HBK2B(3N)

TABLE 2-continued $C_7H_{15}$—[Cy]—$C_2H_4$—[Cy]—[Ph]—C(O)—$(CH_2)_2$—[Ph]—$NO_2$

3HHHBK1B(3N)

$C_3H_7$—[Cy]—[Cy]—[Cy]—[Ph]—C(O)—$CH_2$—[Ph]—$NO_2$

| | |
|---|---|
| 1HBKB(3N) | 7HHH3HBKB(3N) |
| 5HBKB(3N) | 2HHH4HBKB(3N) |
| 7HBKB(3N) | 3HHH4HBKB(3N) |
| 3HHBKB(3N) | 5HHH4HBKB(3N) |
| 5HHBKB(3N) | 1HHH5HBKB(3N) |
| 10HHBKB(3N) | 4HHH5HBKB(3N) |
| 3HHHBKB(3N) | 9HHH5HBKB(3N) |
| 6HHHBKB(3N) | 2HHH3HBKB(3N) |
| 8HHHBKB(3N) | 4HHH3HBKB(3N) |
| 1HHHHBKB(3N) | 7HHH3HBKB(3N) |
| 5HHHHBKB(3N) | 1HBKB(2N) |
| 7HHHHBKB(3N) | 5HBKB(2N) |
| 2H1HBKB(3N) | 7HBKB(2N) |
| 5H1HBKB(3N) | 3HBKB(1N) |
| 9H1HBKB(3N) | 4HBKB(1N) |
| 1H2HBKB(3N) | 8HBKB(1N) |
| 5H2HBKB(3N) | 1HHBKB(2N) |
| 7H2HBKB(3N) | 5HHBKB(2N) |
| 2H3HBKB(3N) | 7HHBKB(2N) |
| 5H3HBKB(3N) | 2HHBKB(1N) |
| 6H3HBKB(3N) | 3HHBKB(1N) |
| H4HBKB(3N) | 7HHBKB(1N) |
| 4H4HBKB(3N) | HHHBKB(2N) |
| 7H4HBKB(3N) | 3HHHBKB(2N) |
| 1H5HBKB(3N) | 7HHHBKB(2N) |
| 5H5HBKB(3N) | 1HHHBKB(1N) |
| 8H5HBKB(3N) | 5HHHBKB(1N) |
| 1HH1HBKB(3N) | 7HHHBKB(1N) |
| 5HH1HBKB(3N) | 2HHHHBKB(2N) |
| 8HH1HBKB(3N) | 3HHHHBKB(2N) |
| 2HH2HBKB(3N) | 7HHHHBKB(2N) |
| 5HH2HBKB(3N) | 1HHHHBKB(1N) |
| 7HH2HBKB(3N) | 4HHHHBKB(1N) |
| 3HH3HBKB(3N) | 8HHHHBKB(1N) |
| 6HH3HBKB(3N) | 2H1HBKB(2N) |
| 11HH3HBKB(3N) | 4H1HBKB(2N) |
| 4HH4HBKB(3N) | 7H1HBKB(2N) |
| 5HH4HBKB(3N) | 1H1HBKB(1N) |
| 7HH4HBKB(3N) | 5H1HBKB(1N) |
| 2HH5HBKB(3N) | 7H1HBKB(1N) |
| 5HH5HBKB(3N) | 2H2HBKB(2N) |
| 8HH5HBKB(3N) | 3H2HBKB(2N) |
| 1HHH1HBKB(3N) | 4H2HBKB(2N) |
| 4HHH1HBKB(3N) | 3H2HBKB(1N) |
| 10HHH1HBKB(3N) | 5H2HBKB(1N) |
| 3HHH2HBKB(3N) | 7H2HBKB(1N) |
| 5HHH2HBKB(3N) | 2H3HBKB(2N) |
| 6HHH2HBKB(3N) | 3H3HBKB(2N) |
| 2HHH3HBKB(3N) | 4H3HBKB(2N) |
| 4HHH3HBKB(3N) | 4H3HBKB(1N) |

6H3HBKB(1N)
9H3HBKB(1N)
2H4HBKB(2N)
5H4HBKB(2N)
7H4HBKB(2N)
1H4HBKB(1N)
8H4HBKB(1N)
12H4HBKB(1N)
2H5HBKB(2N)
3H5HBKB(2N)
4H5HBKB(2N)
4H5HBKB(1N)
6H5HBKB(1N)
9H5HBKB(1N)
2HH1HBKB(2N)
3HH1HBKB(2N)
4HH1HBKB(2N)
4HH2HBKB(1N)
6HH2HBKB(1N)
9HH2HBKB(1N)
2HH3HBKB(2N)
5HH3HBKB(2N)
7HH3HBKB(2N)
3HH4HBKB(1N)
6HH4HBKB(1N)
10HH4HBKB(1N)
1HH5HBKB(2N)
5HH5HBKB(2N)
6HH5HBKB(2N)
3HHH1HBKB(1N)
4HHH1HBKB(1N)
5HHH1HBKB(1N)
1HHH2HBKB(2N)
3HHH2HBKB(2N)
8HHH2HBKB(2N)
2HHH3HBKB(1N)
5HHH3HBKB(1N)
8HHH3HBKB(1N)
1HHH4HBKB(2N)
6HHH4HBKB(2N)
9HHH4HBKB(2N)
2HHH5HBKB(1N)
3HHH5HBKB(1N)
5HHH5HBKB(1N)
1HBK1B(3N)
5HBK1B(3N)
7HBK1B(3N)
3HHBK1B(3N)
5HHBK1B(3N)
10HHBK1B(3N)
3HHHBK1B(3N)
6HHHBK1B(3N)
8HHHBK1B(3N)
1HHHHBK1B(3N)
5HHHHBK1B(3N)
7HHHHBK1B(3N)
2H1HBK1B(3N)
5H1HBK1B(3N)
9H1HBK1B(3N)
1H2HBK1B(3N)
5H2HBK1B(3N)
7H2HBK1B(3N)
2H3HBK1B(3N)
5H3HBK1B(3N)
6H3HBK1B(3N)
H4HBK2B(3N)
4H4HBK1B(3N)
7H4HBK1B(3N)
1H5HBK1B(3N)
5H5HBK1B(3N)
8H5HBK1B(3N)
1HH1HBK1B(3N)
5HH1HBK1B(3N)
8HH1HBK1B(3N)
2HH2HBK1B(3N)
5HH2HBK1B(3N)
7HH2HBK1B(3N)
3HH3HBK1B(3N)
6HH3HBK1B(3N)
11HH3HB1KB(3N)
4HH4HBK1B(3N)
5HH4HBK1B(3N)
7HH4HBK1B(3N)
2HH5HBK1B(3N)
5HH5HBK1B(3N)
8HH5HBK1B(3N)
1HHH1HBK1B(3N)
4HHH1HBK1B(3N)
10HHH1HBK1B(3N)
3HHH2HBK1B(3N)
5HHH2HBK1B(3N)
6HHH2HBK1B(3N)
2HHH3HBK1B(3N)
4HHH3HBK1B(3N)
7HHH3HBK1B(3N)
2HHH4HBK1B(3N)
3HHH4HBK1B(3N)
5HHH4HBK1B(3N)
1HHH5HBK1B(3N)
4HHH5HBK1B(3N)
9HHH5HBK1B(3N)
2HHH3HBK1B(3N)
4HHH3HBK1B(3N)
7HHH3HBK1B(3N)
1HBK2B(3N)
5HBK2B(3N)
7HBK2B(3N)
3HHBK2B(3N)
5HHBK2B(3N)
10HHBK2B(3N)
3HHHBK2B(3N)
6HHHBK2B(3N)
8HHHBK2B(3N)
1HHHHBK2B(3N)
5HHHHBK2B(3N)
7HHHHBK2B(3N)
2H1HBK2B(3N)
5H1HBK2B(3N)
9H1HBK2B(3N)
1H2HBK2B(3N)
5H2HBK2B(3N)
7H2HBK2B(3N)
2H3HBK2B(3N)
5H3HBK2B(3N)
6H3HBK2B(3N)
H4HBK2B(3N)
4H4HBK2B(3N)
7H4HBK2B(3N)
1H5HBK2B(3N)
5H5HBK2B(3N)
8H5HBK2B(3N)
1HH1HBK2B(3N)
5HH1HBK2B(3N)
8HH1HBK2B(3N)

HBK2B(3N)
5HH2HBK2B(3N)
7HH2HBK2B(3N)
3HH3HBK2B(3N)
6HH3HBK2B(3N)
11HH3HBK2B(3N)
4HH4HBK2B(3N)
5HH4HBK2B(3N)
7HH4HBK2B(3N)
2HH5HBK2B(3N)
5HH5HBK2B(3N)
8HH5HBK2B(3N)
1HHH1HBK2B(3N)
4HHH1HBK2B(3N)
10HHH1HBK2B(3N)
3HHH2HBK2B(3N)
5HHH2HBK2B(3N)
6HHH2HBK2B(3N)
2HHH3HBK2B(3N)
4HHH3HBK2B(3N)
7HHH3HBK2B(3N)
2HHH4HBK2B(3N)
3HHH4HBK2B(3N)
5HHH4HBK2B(3N)
1HHH5HBK2B(3N)
4HHH5HBK2B(3N)
9HHH5HBK2B(3N)
2HHH3HBK2B(3N)
4HHH3HBK2B(3N)
7HHH3HBK2B(3N)
1HBK3B(3N)
5HBK3B(3N)
7HBK3B(3N)
3HHBK3B(3N)
5HHBK3B(3N)
10HHBK3B(3N)
3HHHBK3B(3N)
6HHHBK3B(3N)
8HHHBK3B(3N)
1HHHHBK3B(3N)
5HHHHBK3B(3N)
7HHHHBK3B(3N)
2H1HBK3B(3N)
5H1HBK3B(3N)
9H1HBK3B(3N)
1H2HBK3B(3N)
5H2HBK3B(3N)
7H2HBK3B(3N)
2H3HBK3B(3N)
5H3HBK3B(3N)
6H3HBK3B(3N)
H4HBK3B(3N)
4H4HBK3B(3N)
7H4HBK3B(3N)
1H5HBK3B(3N)
5H5HBK3B(3N)
8H5HBK3B(3N)
1HH1HBK3B(3N)
5HH1HBK3B(3N)
8HH1HBK3B(3N)
2HH2HBK3B(3N)
5HH2HBK3B(3N)
7HH2HBK3B(3N)
3HH3HBK3B(3N)
6HH3HBK3B(3N)
11HH3HBK3B(3N)
4HH4HBK3B(3N)
5HH4HBK3B(3N)
7HH4HBK3B(3N)
2HH5HBK3B(3N)
5HH5HBK3B(3N)
8HH5HBK3B(3N)
1HHH1HBK3B(3N)
4HHH1HBK3B(3N)
10HHH1HBK3B(3N)
3HHH2HBK3B(3N)
5HHH2HBK3B(3N)
6HHH2HBK3B(3N)
2HHH3HBK3B(3N)
4HHH3HBK3B(3N)
7HHH3HBK3B(3N)
2HHH4HBK3B(3N)
3HHH4HBK3B(3N)
5HHH4HBK3B(3N)
1HHH5HBK3B(3N)
4HHH5HBK3B(3N)
9HHH5HBK3B(3N)
2HHH3HBK3B(3N)
4HHH3HBK3B(3N)
7HHH3HBK3B(3N)
1HBK4B(3N)
5HBK4B(3N)
7HBK4B(3N)
3HHBK4B(3N)
5HHBK4B(3N)
10HHBK4B(3N)
3HHHBK4B(3N)
6HHHBK4B(3N)
8HHHBK4B(3N)
1HHHHBK4B(3N)
5HHHHBK4B(3N)
7HHHHBK4B(3N)
2H1HBK4B(3N)
5H1HBK4B(3N)
9H1HBK4B(3N)
1H2HBK4B(3N)
5H2HBK4B(3N)
7H2HBK4B(3N)
2H3HBK4B(3N)
5H3HBK4B(3N)
6H3HBK4B(3N)
H4HBK4B(3N)
4H4HBK4B(3N)
7H4HBK4B(3N)
1H5HBK4B(3N)
5H5HBK4B(3N)
8H5HBK4B(3N)
1HH1HBK4B(3N)
5HH1HBK4B(3N)
8HH1HBK4B(3N)
2HH2HBK4B(3N)
5HH2HBK4B(3N)
7HH2HBK4B(3N)
3HH3HBK4B(3N)
6HH3HBK4B(3N)
11HH3HB4KB(3N)
4HH4HBK4B(3N)
5HH4HBK4B(3N)
7HH4HBK4B(3N)
2HH5HBK4B(3N)
5HH5HBK4B(3N)
8HH5HBK4B(3N)
1HHH1HBK4B(3N)
4HHH1HBK4B(3N)

10HHH1HBK4B(3N)
3HHH2HBK4B(3N)
5HHH2HBK4B(3N)
6HHH2HBK4B(3N)
2HHH3HBK4B(3N)
4HHH3HBK4B(3N)
7HHH3HBK4B(3N)
2HHH4HBK4B(3N)
3HHH4HBK4B(3N)
5HHH4HBK4B(3N)
1HHH5HBK4B(3N)
4HHH5HBK4B(3N)
9HHH5HBK4B(3N)
2HHH3HBK4B(3N)
4HHH3HBK4B(3N)
7HHH3HBK4B(3N)
1OHBKB(3N)
5OHBKB(3N)
6OHBK1B(3N)
3OHHBKB(3N)
4OHHBK2B(3N)
1OH1HBKB(3N)
5OH1HBK1B(3N)
7OH2HBK2B(3N)
4OH2HBK2B(3N)
9OH1HBKB(3N)

The production processes for the diamino compound of the present invention and the cyclohexylphenylcarbonyl compound which is the intermediate thereof shall specifically be explained. In the present invention, the compounds shall be shown below using the acronyms shown in Table 1 and Table 2.

The cyclohexylbenzene derivative represented by Formula (3) which is used in the production process of the present invention can readily be synthesized by such publicly known methods as the Grignard reaction of a Grignard reagent obtained from bromobenzene and magnesium with cyclohexanes and reduction carried out by dehydration and hydrogenation. Further, commercial products can be purchased. Specific examples of the cyclohexylbenzene derivatives shall be shown below.

HB, 1HB, 2HB, 3HB, 4HB, 5HB, 6HB, 7HB, 8HB, 9HB, 10HB, 11HB, 12HB, HHB, 1HHB, 2HHB, 3HHB, 4HHB, 5HHB, 6HHB, 7HHB, 8HHB, 9HHB, 10HHB, 11HHB, 12HHB, HHHB, 1HHHB, 2HHHB, 3HHHB, 4HHHB, 5HHHB, 6HHHB, 7HHHB, 8HHHB, 9HHHB, 10HHHB, 11HHHB, 12HHHB,

H1HB, 1H1HB, 2H1HB, 3H1HB, 4H1HB, 5H1HB, 6H1HB, 7H1HB, 8H1HB, 9H1HB, 10H1HB, 11H1HB, 12H1HB, HH1HB, 1HH1HB, 2HH1HB, 3HH1HB, 4HH1HB, 5HH1HB, 6HH1HB, 7HH1HB, 8HH1HB, 9HH1HB, 10HH1HB, 11HH1HB, 12HH1HB, HHH1HB, 1HHH1HB, 2HHH1HB, 3HHH1HB, 4HHH1HB, 5HHH1HB, 6HHH1HB, 7HHH1HB, 8HHH1HB, 9HHH1HB, 10HHH1HB, 11HHH1HB, 12HHH1HB,

H2HB, 1H2HB, 2H2HB, 3H2HB, 4H2HB, 5H2HB, 6H2HB, 7H2HB, 8H2HB, 9H2HB, 10H2HB, 11H2HB, 12H2HB, HH2HB, 1HH2HB, 2HH2HB, 3HH2HB, 4HH2HB, 5HH2HB, 6HH2HB, 7HH2HB, 8HH2HB, 9HH2HB, 10HH2HB, 11HH2HB, 12HH2HB, HHH2HB, 1HHH2HB, 2HHH2HB, 3HHH2HB 4HHH2HB, 5HHH2HB, 6HHH2HB, 7HHH2HB, 8HHH2HB, 9HHH2HB, 10HHH2HB, 11HHH2HB, 12HHH2HB,

H3HB, 1H3HB, 2H3HB, 3H3HB, 4H3HB, 5H3HB, 6H3HB, 7H3HB, 8H3HB, 9H3HB, 10H3HB, 11H3HB, 12H3HB, HH3HB, 1HH3HB, 2HH3HB, 3HH3HB, 4HH3HB, 5HH3HB, 6HH3HB, 7HH3HB, 8HH3HB, 9HH3HB, 10HH3HB, 11HH3HB, 12HH3HB, HHH3HB, 1HHH3HB, 2HHH3HB, 3HHH3HB, 4HHH3HB, 5HHH3HB, 6HHH3HB, 7HHH3HB, 8HHH3HB, 9HHH3HB, 10HHH3HB, 11HHH3HB, 12HHH3HB,

H4HB, 1H4HB, 2H4HB, 3H4HB, 4H4HB, 5H4HB, 6H4HB, 7H4HB, 8H4HB, 9H4HB, 10H4HB, 11H4HB, 12H4HB, HH4HB, 1HH4HB, 2HH4HB, 3HH4HB, 4HH4HB, 5HH4HB, 6HH4HB, 7HH4HB, 8HH4HB, 9HH4HB, 10HH4HB, 11HH4HB, 12HH4HB, HHH4HB, 1HHH4HB, 2HHH4HB, 3HHH4HB, 4HHH4HB, 5HHH4HB, 6HHH4HB, 7HHH4HB, 8HHH4HB, 9HHH4HB, 10HHH4HB, 11HHH4HB, 12HHH4HB,

H5HB, 1H5HB, 2H5HB, 3H5HB, 4H5HB, 5H5HB, 6H5HB, 7H5HB, 8H5HB, 9H5HB, 10H5HB, 11H5HB, 12H5HB, HH5HB, 1HH5HB, 2HH5HB, 3HH5HB, 4HH5HB, 5HH5HB, 6HH5HB, 7HH5HB, 8HH5HB, 9HH5HB, 10HH5HB, 11HH5HB, 12HH5HB, HHH5HB, 1HHH5HB, 2HHH5HB, 3HHH5HB, 4HHH5HB, 5HHH5HB, 6HHH5HB, 7HHH5HB, 8HHH5HB, 9HHH5HB, 10HHH5HB, 11HHH5HB, 12HHH5HB,

1OHB, 2OHB, 3OHB, 4OHB, 5OHB, 6OHB, 7OHB, 8OHB, 9OHB, 10OHB, 11OHB, 12OHB, 1OHHB, 2OHHB, 3OHHB, 4OHHB, 5OHHB 6OHHB, 7OHHB, 8OHHB, 9OHHB, 10OHHB, 11OHHB, 12OHHB, 1OHHHB, 2OHHHB, 3OHHHB, 4OHHHB, 5OHHHB, 6OHHHB, 7OHHHB, 8OHHHB, 9OHHHB, 10OHHHB, 11OHHHB, 12OHHHB,

1OH1HB, 2OH1HB, 3OH1HB, 4OH1HB, 5OH1HB, 6OH1HB, 7OH1HB, 8OH1HB, 9OH1HB, 10OH1HB, 11OH1HB, 12OH1HB, 1OHH1HB, 2OHHHB, 3OHH1HB, 4OHH1HB, 5OHH1HB, 6OHH1HB, 7OHH1HB, 8OHH1HB, 9OHH1HB, 10OHH1HB, 11OHH1HB, 12OHH1HB, 1OHHH1HB, 2OHHH1HB, 3OHHH1HB, 4OHHH1HB, 5OHHH1HB, 6OHHH1HB, 7OHHH1HB, 8OHHH1HB, 9OHHH1HB, 10OHHH1HB, 11OHHH1HB, 12OHHH1HB,

1OH2HB, 2OH2HB, 3OH2HB, 4OH2HB, 5OH2HB, 6OH2HB, 7OH2HB, 8OH2HB, 9OH2HB, 10OH2HB, 11OH2HB, 12OH2HB, 1OHH2HB, 2OHH2HB, 3OHH2HB, 4OHH2HB, 5OHH2HB, 6OHH2HB, 7OHH2HB, 8OHH2HB, 9OHH2HB, 10OHH2HB, 11OHH2HB, 12OHH2HB, 1OHHH2HB, 2OHHH2HB, 3OHHH2HB, 4OHHH2HB, 5OHHH2HB, 6OHHH2HB, 7OHHH2HB, 8OHHH2HB, 9OHHH2HB, 10OHHH2HB, 11OHHH2HB, 12OHHH2HB,

1OH3HB, 2OHHB, 3OH3HB, 4OH3HB, 5OH3HB, 6OH3HB, 7OH3HB, 8OH3HB, 9OH3HB, 10OH3HB, 11OH3HB, 12OH3HB, 1OHH3HB, 2OHH3HB, 3OHH3HB, 4OHH3HB, 5OHH3HB, 6OHH3HB, 7OHH3HB, 8OHH3HB, 9OHH3HB, 10OHH3HB, 11OHH3HB, 12OHH3HB, 1OHHH3HB, 2OHHH3HB, 3OHHH3HB, 4OHHH3HB, 5OHHH3HB, 6OHHH3HB, 7OHHH3HB, 8OHHH3HB, 9OHHH3HB, 10OHHH3HB, 11OHHH3HB, 12OHHH3HB,

1OH4HB, 2OH4HB, 3OH4HB, 4OH4HB, 5OH4HB, 6OH4HB, 7OH4HB, 8OH4HB, 9OH4HB, 10OH4HB, 11OH4HB, 12OH4HB, 1OHH4HB, 2OHH4HB, 3OHH4HB, 4OHH4HB, 5OHH4HB, 6OHH4HB, 7OHH4HB, 8OHH4HB, 9OHH4HB, 10OHH4HB, 11OHH4HB, 12OHH4HB, 1OHHH4HB, 2OHHH4HB, 3OHHH4HB, 4OHHH4HB, 5OHHH4HB, 6OHHH4HB, 7OHHH4HB, 8OHHH4HB, 9OHHH4HB, 10OHHH4HB, 11OHHH4HB, 12OHHH4HB,

1OH5HB, 2OH5HB, 3OH5HB, 4OH5HB, 5OH5HB, 6OH5HB, 7OH5HB, 8OH5HB, 9OH5HB, 10OH5HB, 11OH5HB, 12OH5HB, 1OHH5HB, 2OHH5HB, 3OHH5HB, 4OHH5HB, 5OHH5HB, 6OHH5HB,

7OHH5HB, 8OHH5HB, 9OHH5HB, 10OHH5HB, 11OHH5HB, 12OHH5HB, 1OHHH5HB, 2OHHH5HB, 3OHHH5HB, 4OHHH5HB, 5OHHH5HB, 6OHHH5HB, 7OHHH5HB, 8OHHH5HB, 9OHHH5HB, 10OHHH5HB, 11OHHH5HB, 12OHHH5HB

The acid halide represented by Formula (4) which is used in the production process of the present invention can readily be synthesized by a publicly known method in which a carboxylic acid derivative having nitrobenzene is reacted with thionyl chloride, or commercial products can be purchased.

Specific examples of the acid halide include 4-nitrobenzoyl chloride, 4-nitrobenzoyl bromide, 4-nitrophenylacetyl chloride, 4-nitrophenylacetyl bromide, 4-nitrophenylpropionyl chloride, 4-nitrophenylpropionyl bromide, 4-nitrophenylbutyryl chloride, 4-nitrophenylbutyryl bromide, 4-nitrophenylvaleryl chloride, 4-nitrophenylvaleryl bromide, 4-nitrophenylhexanoyl chloride, 4-nitrophenylhexanoyl bromide, 3-nitrobenzoyl chloride, 3-nitrobenzoyl bromide, 3-nitrophenylacetyl chloride, 3-nitrophenylacetyl bromide, 3-nitrophenylpropionyl chloride, 3-nitrophenylpropionyl bromide, 3-nitrophenylbutyryl chloride, 3-nitrophenylbutyryl bromide, 3-nitrophenylvaleryl chloride, 3-nitrophenylvaleryl bromide, 3-nitrophenylhexanoyl chloride, 3-nitrophenylhexanoyl bromide, 2-nitrobenzoyl chloride, 2-nitrobenzoyl bromide, 2-nitrophenylacetyl chloride, 2-nitrophenylacetyl bromide, 2-nitrophenylpropionyl chloride, 2-nitrophenylpropionyl bromide, 2-nitrophenylbutyryl chloride, 2-nitrophenylbutyryl bromide, 2-nitrophenylvaleryl chloride, 2-nitrophenylvaleryl bromide, 2-nitrophenylhexanoyl chloride, and 2-nitrophenylhexanoyl bromide.

A catalyst is usually used for the Friedel-Crafts reaction of the cyclohexylbenzene derivative represented by Formula (3) with the acid halide represented by Formula (4). The catalyst includes $AlCl_3$, $SbCl_5$, $FeCl_3$, $TeCl_2$, $SnCl_4$, $TiCl_4$, $BiCl_3$ and $ZnCl_2$. $AlCl_3$ and $FeCl_3$ are preferred from the viewpoint of a reactivity, a safety and a profitability.

Further, solvents such as carbon disulfide, dichloromethane, chloroform, dichloroethane and nitrobenzene are usually used in the reaction.

The reaction is carried out by mixing the catalyst with the acid halide in a solvent while stirring and adding dropwise the cyclohexylbenzene derivative (in the form of a solution, if necessary) at 0 to 150° C. to react them. In a certain case, the reaction may be carried out by mixing the catalyst with the cyclohexylbenzene derivative in the solvent while stirring and adding dropwise the acid halide (dissolved in a solvent, if necessary) at 0 to 150° C. to react them. Or, the reaction is carried out in some cases by mixing the cyclohexylbenzene derivative with the acid halide in the solvent while stirring and adding the catalyst at 0 to 150° C. to react them.

After finishing the reaction, the reaction mixed solution is poured into ice in order to decompose the adduct of the product and the catalyst, and the solvent is removed by washing with water and distillation or steam distillation to refine the product, whereby obtained is the cyclohexylphenylcarbonyl compound (hereinafter referred to as a compound II) represented by Formula (5).

Conc. sulfuric acid and conc. nitric acid are usually used for carrying out nitration of this compound II. In carrying out the reaction, no solvent or chloroform is used. The reaction is carried out by mixing the compound II with conc. sulfuric acid while stirring and slowly adding dropwise conc. nitric acid in an ice bath to react them.

After finishing the reaction, the reaction mixed solution is poured into ice and extracted with an organic solvent. Then, washing with water is carried out, and the solvent is removed to refine the product, whereby the compound represented by Formula (6) (hereinafter referred to as a compound III) is obtained.

The carbonyl group of the compound III can be reduced by reacting triallylalkyl silane, to be specific, triethyl silane in the presence of a catalyst such as trifloromethanesulfonic acid, titanium tetrachloride and boron trifluoride or a complex thereof. In this case, the reaction temperature falls preferably between 0 to 100° C. In carrying out the reaction, a solvent may be used, and halogenated hydrocarbons such as dichloromethane, chloroform and dichloroethane are preferred.

With respect to the refining method, the dinitro compound represented by Formula (7) can be obtained by a column chromatography in which alumina or silica gel is used and ethyl acetate, toluene or chloroform is further used as a solvent and a recrystallization method in which ethyl acetate, toluene or heptane is used.

This dinitro compound represented by Formula (7) can be reduced by carrying out hydrogen reduction in a solvent such as toluene, xylene, methanol, ethanol, ethylene glycol monoethyl ether, ethylene glycol monobutyl ether, ethyl acetate, tetrahydrofuran and acetic acid at an atmospheric pressure or under application of pressure at 10 to 80° C. by using a catalyst such as platinum.carbon, platinum oxide, Raney nickel and palladium.carbon and adding, if necessary, an acid such as acetic acid, hydrochloric acid, sulfuric acid, phosphoric acid, oxalic acid and trifluroacetic acid.

The compound III represented by Formula (6) can be reduced as well by hydrogen reduction of the carbonyl group and the nitro group. That is, hydrogen reduction is carried out in a solvent such as toluene, xylene, methanol, ethanol, ethylene glycol monoethyl ether, ethylene glycol monobutyl ether, ethyl acetate, tetrahydrofuran and acetic acid under application of pressure at 80 to 100° C. by using a catalyst such as platinum-carbon, platinum oxide, Raney nickel and palladium-carbon and adding, if necessary, an acid such as acetic acid, hydrochloric acid, sulfuric acid, phosphoric acid, oxalic acid and trifluroacetic acid.

With respect to the refining method, the compound represented by Formula (1) can be obtained by a column chromatography in which alumina or silica gel is used and ethyl acetate, toluene or chloroform is further used as a solvent and a recrystallization method in which ethyl acetate, toluene or heptane is used.

The targeted diamino compound can be produced by suitably selecting the substituents $A_1$ and $A_2$, m and n in Formulas (3) and (4) described above.

The diamino compound of the present invention can be used as a raw material of a polyimide for a liquid crystal alignment film, and in addition thereto, making use of a characteristic of the diamino compound having a relatively weak polarity, it can be used for various polyimide coating agents, polyimide-molded articles, films and fibers. Further, it can be used as a raw material for polyamide, polyamide-imide and urea resins, or a curing agent for epoxy resins.

EXAMPLES

The compound of the present invention shall be explained below in further details with reference to examples, and products obtained by using this compound, that is, a liquid crystal alignment film of a polyimide shall be shown as an application example. However, the present invention shall not be restricted to these examples.

In the application examples shown below, the degree of burning was determined using a C-V curve method. In the C-V curve method, an alternating current of 25 mV and 1 kHz is applied to a liquid crystal cell, and a chopping wave (hereinafter referred to as a DV voltage) of a direct current of 0.0036 Hz is superposedly applied, wherein a capacity C which is changed by sweeping the DC voltage in a range of −10 V to 10 V is recorded.

The DC voltage is swept to a positive side (0→10 V), and the capacity grows large. Next, when it is swept to a negative side (10→0 V), the capacity is reduced. When it is swept to more negative side than 0 (0→−10 V), the capacity increases again, and when it is swept to a positive side (−10→0 V), the capacity is reduced again. When this is repeated in several cycles, a wave form as shown in FIG. 1 is obtained. A deviation of a charge is produced on the surface of the liquid crystal alignment film, and when this deviation is stabilized, the voltage draws a hysteresis curve in both positive and negative sides as shown in FIG. 1.

Based on this FIG. 1, tangential lines toward the respective C-V curves and a straight line showing the capacity ($C_0$) when the DC voltage is zero are drawn. Then, the respective intersection points ($\alpha1$ to $\alpha4$) thereof were determined, and voltage differences between the respective two points of $|\alpha1-\alpha2|$ in the positive side and $|\alpha3-\alpha4|$ in the negative side were determined. An average voltage difference thereof was determined according to the following equation to obtain a residual charge:

$$\text{residual charge}=(|\alpha1-\alpha2|+|\alpha3-\alpha4|)/2$$

The residual charge can be used as a parameter for showing a deviation of a charge and a stabilization thereof if measured on the condition that the liquid crystal cells have the same thickness and the alignment films have the same thickness. That is, if an alignment film having less residual charge is used, burning can be reduced more.

Figure 2:
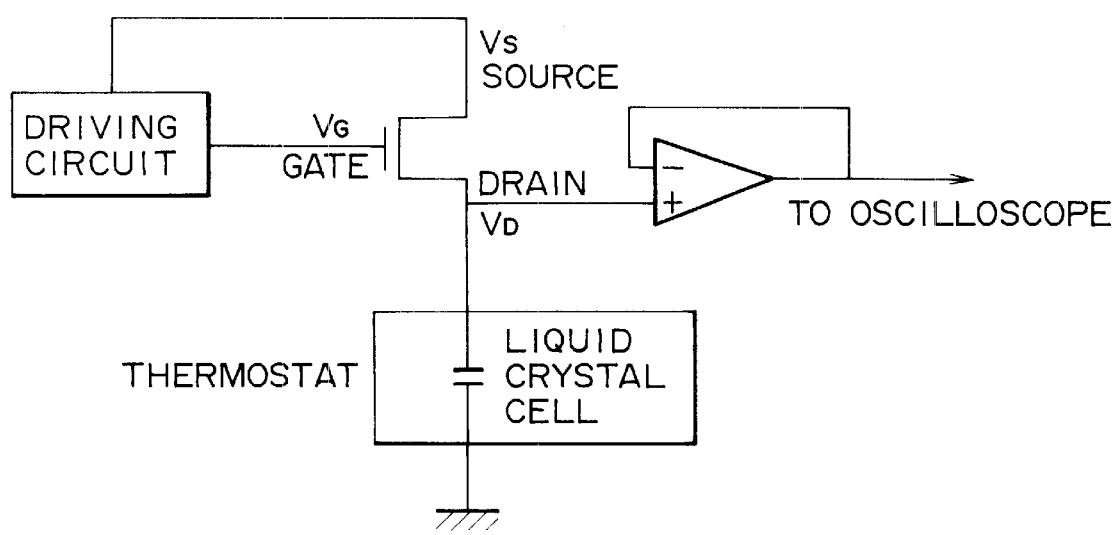
FIG. 2 is a circuit diagram of a measuring apparatus for a voltage-holding rate.

The voltage-holding rate was measured in a circuit shown in FIG. 2. It was measured by a method in which the drain (VD) which was changed by applying a short wave form (Vs) having a gate pulse width of 69 μs, a frequency of 30 Hz and a wave height of ±4.5 V to a source was read on an oscilloscope. For example, when a positive short wave form is applied to the source, the drain (VD) continues to show a positive value until a negative short wave form is applied next time.

Figure 3:
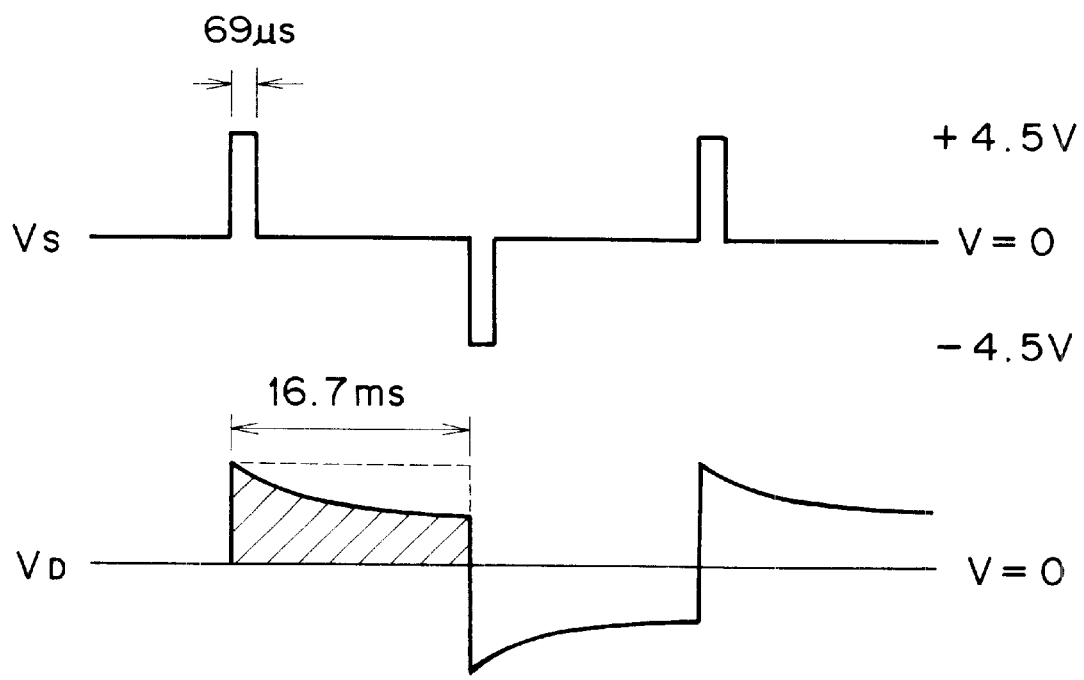
FIG. 3 is a drawing showing a short wave form (Vs) which is applied to a source and a variable drain (VD) which is read from an oscilloscope.

If the voltage-holding rate is 100%, the VD shown in FIG. 3 takes a rectangular orbit shown by a dotted line, but the VD takes usually an orbit shown by a solid line which comes gradually close to zero.

Then, the measured area of the orbit (area surrounded by V=0 and the orbit), that is, an obliquely-lined part was calculated, and this was repeated four times to obtain the average value. The area observed when the voltage was not reduced at all was set at 100%, and the voltage-holding rate (%) was shown by a relative value of the measured area based on the above area.

The pretilt angle was determined by a crystal rotation method.

EXAMPLE 1

1-(4-Pentylcyclohexyl)-4-[4-(4'-amino)benzyl-2-amino] phenylcyclohexane was produced according to the following procedure.

(a) Production of 1-(4-pentylcyclohexyl)-4-(4-nitrobenzoylphenyl)cyclohexane A three neck flask equipped with a stirrer, a thermometer and a nitrogen-substituting apparatus was charged with 51 g (384 millimole) of aluminum chloride and 150 ml of dichloromethane, and 39 g (211 millimole) of 4-nitrobenzoyl chloride was added to this mixed solution while cooling with ice to dissolve them. Further, a solution obtained by dissolving 10 g (52.1 millimole) of 1-phenyl-4-(4-pentylcyclohexyl)cyclohexane in 150 ml of dichloromethane was dropwise added thereto in one hour. After finishing adding, the solution was stirred at a room temperature for 2 hours.

After confirming the completion of the reaction by means of liquid chromatography, the reaction solution was poured into 2 liters of ice and water, and then the product was extracted with 3 liters of chloroform. The extract was washed with a 6N-HCl aqueous solution, a sodium hydrogencarbonate aqueous solution, a brine and water and then dried on magnesium sulfate. Next, chloroform was removed by means of a rotary evaporator, and after confirming that crystals were sufficiently deposited, they were filtered. The filtered cake was recrystallized and refined in a mixed solution of toluene and heptane to obtain 65 g of the crystals of 1-(4-pentylcyclohexyl)-4-(4-nitrobenzoylphenyl) cyclohexane.

(b) Synthesis of 1-(4-pentylcyclohexyl)-4-(4-nitrobenzoyl-2-nitrophenyl)cyclohexane A three neck flask equipped with a stirrer, a thermometer and a nitrogen-substituting apparatus was charged with 65 g (141 millimole) of 1-(4-pentylcyclohexyl)-4-(4-nitrobenzoylphenyl)cyclohexane and 300 ml of conc. sulfuric acid, and 100 ml of conc. nitric acid was dropwise added to this mixed solution in one hour while cooling with ice. After finishing adding, the solution was stirred for 3 hours.

After confirming the completion of the reaction by means of liquid chromatography, the reaction solution was poured into one liter of ice and water, and then the product was extracted with 2 liters of chloroform. The extract was washed with a sodium hydrogencarbonate aqueous solution, a brine and water and then dried on magnesium sulfate. Next, chloroform was removed by means of a rotary evaporator, and after confirming that crystals were sufficiently deposited, they were filtered. The filtered cake was recrystallized and refined in heptane to obtain 50 g of the crystals of 1-(4-pentylcyclohexyl)-4-(4-nitrobenzoyl-2-nitrophenyl)cyclohexane. ( c) Synthesis of 1-(4-pentylcyclohexyl)-4-(4-nitrobenzyl-2-nitrophenyl)cyclohexane A three neck flask equipped with a stirrer, a thermometer and a nitrogen-substituting apparatus was charged with 50 g (99 millimole) of 1-(4-pentylcyclohexyl)-4-(4-nitrobenzoyl-2-nitrophenyl)cyclohexane and 300 ml of chloroform, and 47 g (247 millimole) of titanium tetrachloride was dropwise added to this mixed solution in 30 minutes while cooling with ice, and subsequently 57 g (494 millimole) of triethyl silane was dropwise added in one hour. After finishing adding, the solution was left coming back to a room temperature and stirred for 3 hours.

After confirming the completion of the reaction by means of liquid chromatography, the reaction solution was poured into one liter of ice and water, and then the product was extracted with 2 liters of chloroform. This extract was washed with a sodium hydrogencarbonate aqueous solution, a brine and water and then dried on magnesium sulfate. Next, chloroform was removed by means of a rotary evaporator, and after confirming that crystals were sufficiently deposited, they were filtered. The filtered cake was recrystallized and refined in a mixed solution of toluene and heptane to obtain 32 g of the crystals of 1-(4-pentylcyclohexyl)-4-(4-nitrobenzyl-2-nitrophenyl)cyclohexane. ( d) Production of 1-(4-pentylcyclohexyl)-4-[4-(4'-amino)benzyl-2-amino]phenylcyclohexane A flask of 1 liter equipped with a stirrer and a nitrogen-substituting apparatus was charged with 32 g (65 millimole) of 1-(4-pentylcyclohexyl)-4-(4-nitrobenzyl-2-nitrophenyl)cyclohexane, 1.6 g of a Pd-C catalyst (5% grade, moisture content: 55.9%) and a mixed solvent of 120 ml of toluene and 60 ml of ethanol, and the solution was contacted with hydrogen gas at an atmospheric pressure while stirring. After absorption of hydrogen was stopped, the catalyst contained in the reaction solution was filtered off. The condensation product of the resulting filtrate was dissolved in a mixed solution of chloroform and ethyl acetate and subjected to column chromatographic treatment with active alumina. Further, the resulting product was recrystallized and refined in a mixed solution of toluene and heptane to obtain 19 g of the crystals of 1-(4-pentylcyclohexyl)-4-[4-(4'-amino)benzyl-2-amino]phenylcyclohexane. The peak of the molecular weight 432 of this compound was confirmed by means of GC-MS.

EXAMPLE 2

The Friedel-Crafts reaction of 1-phenyl-4-(4-heptylcyclohexylethyl)cyclohexane {7H2HB} with 4-nitrobenzoyl chloride, nitration, a reduction of the carbonyl group and a reduction to the amino group were carried out by the same method as in Example 1, whereby produced was 1-(4-heptylcyclohexyl)-4-[4-(4'-amino)benzyl-2-amino]phenylcyclohexane which was represented by {7H2HB(4A)1B(3A)}.

EXAMPLE 3

The Friedel-Crafts reaction of 1-phenyl-4-(4-propylcyclohexyl)cyclohexylcyclohexane {3HHHB} with 4-nitrobenzoyl chloride, nitration, a reduction to the carbonyl group and a reduction to the amino group were carried out by the same method as in Example 1, whereby produced was 1-[4-(4-propylcyclohexyl)cyclohexyl]-4-[4-(4'-amino)benzyl-2-amino]phenylcyclohexane which was represented by {3HHHB(4A)1B(3A)}.

Application Example 1

A four neck flask of 1000 ml equipped with a stirrer, a thermometer, a condenser and a nitrogen-substituting apparatus was charged with 135.00 g of N-methyl-2-pyrrolidone which was dehydrated and refined and then 3.18 g of 4,4'-diaminodiphenylethane and 6.48 g of 1-(4-pentylcyclohexyl)-4-(4-aminobenzyl-2-aminophenyl)cyclohexane and stirred under dry nitrogen flow to dissolve them. Added was 6.54 g of pyromellitic dianhydride while maintaining the temperature of the solution at 5 to 70° C. to react them for 5 to 30 hours, and then a 1:1 solvent of γ-butyrolactone and butyl cellosolve was added to obtain a polyamic acid solution (a) having a polymer concentration of 6%.

When the temperature was elevated by reaction heat during the reaction, the reaction was carried out while controlling the reaction temperature to about 70° C. or lower. In the application example of the present invention, the reaction was carried out while checking the viscosity of the polyamic acid solution during the reaction, and the reaction was finished when the viscosity after adding the whole solvent became 55 to 60 mPa·s (determined by means of an E type viscometer at 25° C). The polyamic acid solution (a) thus obtained was stored at a low temperature.

This polyamic acid solution was applied on a transparent glass substrate having an ITO electrode provided on one face thereof by a rotational application method (spinner method). After the solution was applied in 15 seconds on a revolution condition of 5000 rpm, it was dried at 100° C. for 10 minutes. Then, the temperature was elevated up to 200° C. in one hour in an oven, and heat treatment was carried out at 200° C. for 90 minutes to obtain a polyimide film having a film thickness of about 60 nm.

The coated surfaces of two substrates on which the polyimide films were formed were subjected respectively to rubbing treatment to prepare liquid crystal alignment films.

These liquid crystal alignment films were disposed oppositely to each other so that the rubbing directions were parallel to form a liquid crystal cell having a cell thickness of 20 micron, and liquid crystal for TFT ("FB01" manufactured by Chisso Co., Ltd.) was sealed therein. After sealing, the cell was subjected to isotropic treatment at 120° C. for 30 minutes and slowly cooled down to a room temperature to obtain a liquid crystal element. This liquid crystal element had a pretilt angle of 6.1° at 25° C. Also, this cell had a residual charge of 0.05 V at 25° C. and a holding rate of 98.5%.

Further, after sealing, the cell was subjected to isotropic treatment at 120° C. for 72 hours and slowly cooled down to a room temperature to obtain a liquid crystal element. This liquid crystal element had a pretilt angle of 5.9° at 25° C.

Application Example 2

A four neck flask of 1000 ml equipped with a stirrer, a thermometer, a condenser and a nitrogen-substituting apparatus was charged with 159.20 g of N-methyl-2-pyrrolidone which was dehydrated and refined, then 6.09 g of 1,3-bis (4-(4-aminobenzyl)phenyl)propane and 6.48 g of 1-(4-pentylcyclohexyl)-4-(4-aminobenzyl-2-aminophenyl)cyclohexane and stirred under dry nitrogen flow to dissolve them. Added was 6.54 g of pyromellitic dianhydride while maintaining the temperature of the solution at 5 to 70° C. to react them for 5 to 30 hours, and then a 1:1 solvent of γ-butyrolactone and butyl cellosolve was added to obtain a polyamic acid solution (b) having a polymer concentration of 6%.

When the temperature was elevated by reaction heat during the reaction, the reaction was carried out while controlling the reaction temperature to about 70° C. or lower. In the application example of the present invention, the reaction was carried out while checking the viscosity of the polyamic acid solution during the reaction, and the reaction was finished when the viscosity after adding the whole solvents became 55 to 60 mPa·s (determined by means of an E type viscometer at 25° C). The polyamic acid solution (b) thus obtained was stored at a low temperature.

This solution was used to obtain a liquid crystal element according to Application Example 1. This liquid crystal element had a pretilt angle of 5.5° at 25° C. Also, this cell had a residual charge of 0.08 V at 25° C. and a holding rate of 98.3%.

Further, after sealing, the cell was subjected to isotropic treatment at 120° C. for 72 hours and slowly cooled down to a room temperature to obtain a liquid crystal element. This liquid crystal element had a pretilt angle of 5.7° at 25° C.

Comparative Application Example 1

A polyamic acid solution was obtained according to Application Example 1, except that in Application Example 1, 7.80 g of 1,1-bis[4-(4-aminophenoxy)phenyl]-4-pentylcyclohexane was substituted for 6.48 g of 1-(4-pentylcyclohexyl)-4-(4-aminobenzyl-2-aminophenyl)cyclohexane.

This polyamic acid solution was used to obtain a liquid crystal element according to Application Example 1. This liquid crystal element had a pretilt angle of 6.0° in the case of isotropic treatment at 120° C. for 30 minutes and 4.9° in the case of isotropic treatment at 120° C. for 72 hours.

Comparative Application Example 2

A polyamic acid solution was obtained according to Application Example 2, except that in Application Example 2, 7.80 g of 1,1-bis[4-(4-aminophenyl ether)phenyl]-4-pentylcyclohexane was substituted for 6.48 g of 1-(4-pentylcyclohexyl)-4-(4-aminobenzyl-2-aminophenoxy)cyclohexane.

This polyamic acid solution was used to obtain a liquid crystal element according to Application. Example 2. This liquid crystal element had a pretilt angle of 4.9° in the case of isotropic treatment at 120° C. for 30 minutes and 6.9° in the case of isotropic treatment at 120° C for 72 hours.

The novel diamino compound and the production process for the same were provided by the present invention.

The diamino compound of the present,invention is excellent as an intermediate raw material for a liquid crystal alignment film. For example, a polyimide compound using the diamino compound of the present invention as a raw material shows an excellent effect as a liquid crystal alignment film. For example, a liquid crystal display element using the above liquid crystal alignment film controls a variation in the pretilt angle even in a long-term test at a high temperature and is turned by conventional rubbing treatment into a liquid crystal display film having a uniform and high pretilt angle over the whole region of a substrate having a wide display area, which is requested to an STN liquid crystal display element.

The diamino compound of the present invention is designed as an intermediate raw material for a liquid crystal alignment film and shows an excellent effect. In addition thereto, it can be used for other high molecular compounds such as polyimide and polyamide and modification thereof and is used for other purposes such as an epoxy cross-linking agent. Further, it can be expected to introduce new characteristics into high molecular compounds.

What is claimed is:

1. A diamino compound represented by Formula (1):

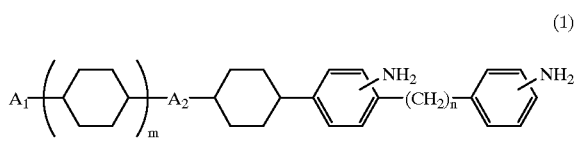

(1)

(wherein $A_1$ represents a hydrogen atom or a linear or branched alkyl group having 1 to 12 carbon atoms, and one or optional methylene groups which are not adjacent in the group may be substituted with an oxygen atom; $A_2$ represents a single bond or an alkylene group having 1 to 5 carbon atoms, and one or optional methylene groups which are not adjacent in the group may be substituted with an oxygen atom; one amino group is bonded to any position in the ring; m represents an integer of 0 to 3, and n represents an integer of 1 to 5).

2. The diamino compound as described in claim 1, wherein said diamino compound is represented by the following Formula (1'):

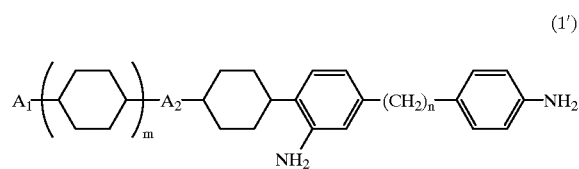

(1')

3. A diamino compound represented by Formula (2):

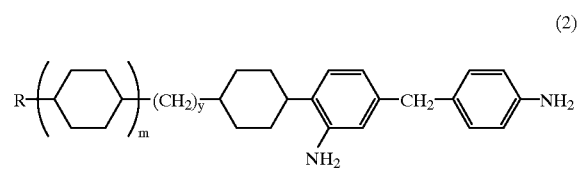

(2)

(wherein R represents a linear or branched alkyl group having 1 to 12 carbon atoms, an alkoxy group having 1 to 11 carbon atoms or a hydrogen atom; m represents an integer of 0 to 3, and y represents an integer of 0 to 5).

4. The diamino compound as described in claim 3, wherein m is 1 to 2, and y is 0 in Formula (2).

5. The diamino compound as described in claim 3, wherein said diamino compound is represented by the following Formula (2'):

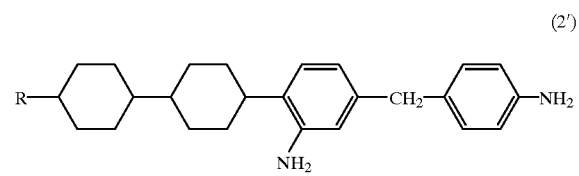

(2')

(wherein R represents a linear or branched alkyl group having 1 to 12 carbon atoms, an alkoxy group having 1 to 11 carbon atoms or a hydrogen atom).

6. A production process for a diamino compound represented by Formula (1):

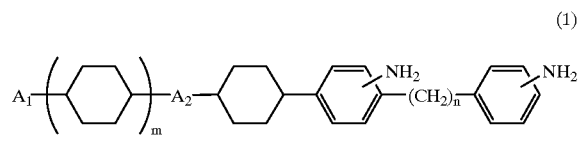

(1)

(wherein $A_1$ represents a hydrogen atom or a linear or branched alkyl group having 1 to 12 carbon atoms, and one or optional methylene groups which are not adjacent in the group may be substituted with an oxygen atom; $A_2$ represents a single bond or an alkylene group having 1 to 5 carbon atoms, and one or optional methylene groups which are not adjacent in the group may be substituted with an oxygen atom; and m represents an integer of 0 to 3; one amino group is bonded to any position in the ring), characterized by reacting a cyclohexylbenzene derivative represented by Formula (3):

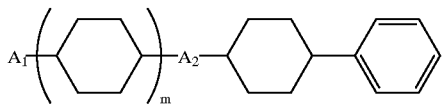
(3)

(wherein the respective marks are synonymous with those described above) with an acid halide represented by Formula (4):

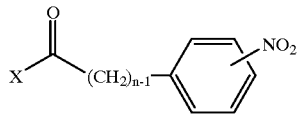
(4)

(wherein X represents any of a bromine atom and a chlorine atom; one nitro group is bonded to any position in the ring; and n represents an integer of 1 to 5) by the Frieldel-Crafts reaction to produce a cyclohexylphenylcarbonyl compound represented by Formula (5):

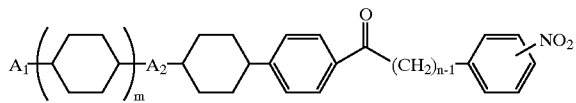
(5)

(wherein the respective marks are synonymous with those described above), and reducing said compound after nitrating.

7. The production process for the diamino compound as described in claim 6, comprising nitrating the cyclohexylphenylcarbonyl compound represented by Formula (5) to synthesize a compound represented by Formula (6):

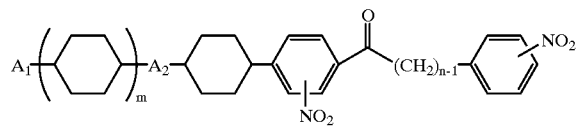
(6)

(wherein the respective marks are synonymous with those described above), then reducing the carbonyl group to thereby synthesize a dinitro compound represented by Formula (7):

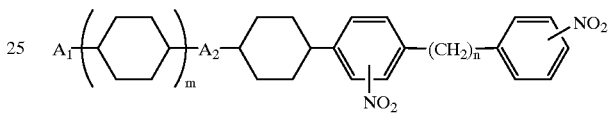
(7)

(wherein the substituents are synonymous with those described above in Formula (6)), and reducing the nitro groups.

* * * * *